United States Patent
Seeger

(10) Patent No.: US 9,760,691 B2
(45) Date of Patent: Sep. 12, 2017

(54) INTERACTIVE ADHERENCE DRUG DISPENSING AND COMMUNICATIONS PLATFORM

(71) Applicant: Empire Technology Development LLC, Wilmington, DE (US)

(72) Inventor: Mark Elard Seeger, New York, NY (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/647,079

(22) PCT Filed: Oct. 1, 2013

(86) PCT No.: PCT/US2013/062894
§ 371 (c)(1),
(2) Date: May 22, 2015

(87) PCT Pub. No.: WO2014/088692
PCT Pub. Date: Jun. 12, 2014

(65) Prior Publication Data
US 2015/0347713 A1    Dec. 3, 2015

Related U.S. Application Data

(60) Provisional application No. 61/732,876, filed on Dec. 3, 2012.

(51) Int. Cl.
*G06F 19/00* (2011.01)
*A61J 7/00* (2006.01)
(Continued)

(52) U.S. Cl.
CPC ........ *G06F 19/3462* (2013.01); *A61J 7/0084* (2013.01); *A61J 7/02* (2013.01);
(Continued)

(58) Field of Classification Search
CPC .. A61J 1/03; A61J 7/0076; A61J 1/035; A61J 7/04; G06F 19/3462
See application file for complete search history.

(56) References Cited

U.S. PATENT DOCUMENTS 7,252,208 B1 *   8/2007   Alvino ............... B65D 83/0463
                                                             221/28
7,295,226 B1 *  11/2007   Meron ............... A61B 1/00036
                                                             348/77
(Continued)

FOREIGN PATENT DOCUMENTS

GB          2489921 A      10/2012
WO   WO 2013086363 A2 *    6/2013   ............. A61B 5/002

OTHER PUBLICATIONS

"Download iTunes Free," accessed at http://web.archive,org/web/20121130144143/http://www.apple.com/itunes/affiliates/download, accessed on Sep. 20, 2014, p. 1.
(Continued)

*Primary Examiner* — Gene Crawford
*Assistant Examiner* — Stephen Akridge
(74) *Attorney, Agent, or Firm* — Turk IP Law, LLC

(57) ABSTRACT

Technologies are generally described for providing a pill dispensing device with adherence monitoring and alerting features, as well as communication capabilities. A pill pack may be integrated within a housing of the pill dispensing device, where removal of each pill in the pill pack may be monitored through a conductive trace or comparable mechanism. Timing of the removal, remaining pills, and similar information may also be detected by the pill dispensing device and provided along with additional information such as health status of the consumer monitored by one or more sensors to a health care provider or similar entity over wired and/or wireless networks. The pill dispensing device may include audio and/or visual output device(s) to provide alerts
(Continued)

and health/medication related information to the consumer. A display technology may employed enabling continuous display with low power usage such as ink display while providing color and/or video capabilities.

20 Claims, 11 Drawing Sheets

(51) Int. Cl.
*A61J 7/02* (2006.01)
*A61J 7/04* (2006.01)
*G06F 21/31* (2013.01)
*H04L 29/06* (2006.01)
*H04W 12/06* (2009.01)
*H04L 29/08* (2006.01)

(52) U.S. Cl.
CPC ........... *A61J 7/0409* (2013.01); *A61J 7/0418* (2015.05); *A61J 7/0436* (2015.05); *A61J 7/0463* (2015.05); *A61J 2200/30* (2013.01); *A61J 2205/70* (2013.01); *G06F 21/31* (2013.01); *H04L 63/0861* (2013.01); *H04L 67/12* (2013.01); *H04W 12/06* (2013.01); *Y02B 60/50* (2013.01)

(56) References Cited

U.S. PATENT DOCUMENTS

| | | | | |
|---|---|---|---|---|
| 8,193,918 | B1* | 6/2012 | Shavelsky | A61J 7/04 340/309.16 |
| 2001/0028308 | A1* | 10/2001 | De La Huerga | A61M 5/14212 340/573.1 |
| 2002/0017996 | A1* | 2/2002 | Niemiec | A61J 7/0481 340/573.1 |
| 2002/0096543 | A1* | 7/2002 | Juselius | A61J 7/0481 222/631 |
| 2005/0241983 | A1* | 11/2005 | Snyder | A61J 7/0481 206/539 |
| 2006/0058917 | A1* | 3/2006 | Vonk | A61J 7/0481 700/236 |
| 2006/0124655 | A1* | 6/2006 | Ratnakar | A61J 7/02 221/3 |
| 2007/0023444 | A1* | 2/2007 | Holloway | A61J 1/03 221/7 |
| 2008/0054007 | A1* | 3/2008 | Mador | A61J 7/0481 221/1 |
| 2009/0167531 | A1* | 7/2009 | Ferguson | G06F 19/3462 340/572.1 |
| 2009/0194434 | A1* | 8/2009 | Ellis | A61J 1/035 206/1.5 |
| 2009/0194452 | A1* | 8/2009 | Hession | A61J 1/035 206/531 |
| 2010/0283601 | A1* | 11/2010 | Tai | G06Q 50/24 340/539.12 |
| 2012/0035760 | A1 | 2/2012 | Portney | |
| 2013/0285681 | A1* | 10/2013 | Wilson | G01N 27/00 324/693 |
| 2013/0310664 | A1* | 11/2013 | Kozloski | A61M 31/00 600/302 |
| 2014/0195100 | A1* | 7/2014 | Lundsgaard | G07C 5/0841 701/29.6 |

OTHER PUBLICATIONS

"FDA Approves Ingestible 'Digital Pill' to Monitor Medication Adherence," accessed at http://web.archive.org/web/20131226030702/http://www.ihealthbeat.org/articles/2012/8/3/fda-approves-ingestible-digital-pill-to-monitor-medication-adherence, published on Aug. 3, 2012, p. 1.
"High definton health," accessed at http://web.archive.org/web/2012041321123/http://www.welfra.me/, accessed on Sep. 20, 2014, pp. 1-2.
"I want to motivate," accessed at http://web.archive.org/web/20120919224717/http://www.healthrally.com/, accessed on Sep. 20, 2014, pp. 1-3.
"Improving medication adherence through individualized intervention targeting," accessed at http://web.archive.org/web/20121130204019/http://allazohealth.com/, accessed on Sep. 20, 2014, p. 1.
"Sessions is your personal health coach, ready to help you lead a more active life right now," accessed at http://web.archive.org/web/20120919074923/https://www.joinsessions.com/, accessed on Sep. 20, 2014, pp. 1-3.
"Reify Health," accessed at http://web.achive.org/web/20121018105848/http://www.reifyhealth.com/, accessed on Sep. 20, 2014, pp. 1-2.
"Mobile Apps," accessed at http://web.archive.org/web/20120315150455/http://rxapps.com/, accessed on Sep. 20, 2014, pp. 1-2.
"Sano Intelligence," accessed at http://web.archive.org/web/20120627043658/http://www.crunchbase.com/company/sano-intelligence, posted on Jun. 18, 2012, p. 1.
"Our Patented Smart Bottle Technology . . . ," accessed at http://web.archive.org/web/20121113233506/http://www.adheretech.com/, accessed on Sep. 20, 2014, p. 1.
"MedQ Remembers So You Wont Have To!"accessed at http://web.archive.org/web/20121025102737/http://lifesavingpillbox.com/, accessed on Sep. 20, 2014 pp. 1-2.
Heussner, K.M., "Mango Health nabs $1.45M to build gamified mobile health apps," accessed at http://web.archive.org/web/20121123232156/http://gigaom.com/2012/08/01/mango-health-nabs-1-45m-to-build-gamified-mobile-health-apps, posted on Aug. 1, 2012, pp. 1-7.
International Search Report and Written Opinion for PCT application No. PCT/US2013/62894 mailed Aug. 12, 2014.
Stomp, W., "Proteus Ingestible Sensor for Tracking Medication Intake Receives FDA Clearance," accessed at http://web.archive.org/web/20120804180313/http://medgadget.com/2012/07/proteus-ingestible-sensor-for-tracking-medication-intake-receives-fda-clearance.html. published on Jul. 31, 2012, pp. 1-3.
Trei, M., "Audio visual pillbox reminds the forgetful to take their meds," accessed at http://www.dvice.com/archives/2012/08/audio-visual-pi.php, published on Aug. 10, 2012, pp. 1-3.

* cited by examiner

INTERACTIVE ADHERENCE DRUG DISPENSING AND COMMUNICATIONS PLATFORM

CROSS-REFERENCE TO RELATED APPLICATIONS

This Application is the U.S. National Stage filing under 35 U.S.C §371 of International Application No. PCT/US13/62894 filed on Oct. 1, 2013, which claims the benefit under 35 U.S.C §119(e) to U.S. Provisional Application No. 61/732,876 filed on Dec. 3, 2012. The International Application and the U.S. Provisional Application are herein incorporated by reference in their entireties.

BACKGROUND

Unless otherwise indicated herein, the materials described in this section are not prior art to the claims in this application and are not admitted to be prior art by inclusion in this section.

With the proliferation of computing and networking technologies, smaller form factor computing devices such as tablets, smart phones, etc. are increasingly used for professional and personal purposes. In the pharmaceutical industry, people take multiple different prescription medicines, and adherence and compliance are challenges for health care professionals. Consumers may not take their medicine when they are supposed to, which can result in poor health for the consumer and poor profitability for the pharmaceutical industry. The pharmaceutical industry may desire to be able to take advantage of the fact that consumers often utilize small computing devices, and the small computing devices may be employed to remind a consumer to take his medication and to track medication consumption. However, the computing device (such as a smart phone) reminding a consumer to take their medication and the consumer actually taking it, are not necessarily connected.

SUMMARY

The present disclosure generally describes techniques for providing an interactive adherence drug dispensing and communications platform.

According to some examples, a pill dispensing device is described. An example pill dispensing device may include a housing, a memory adapted to store instructions, a processor adapted to execute the instructions stored on the memory, a communication module configured to facilitate communication with one or more sources for exchanging pill consumption and user data, a printed circuit board configured to support one or more of the memory, the processor, and circuitry associated with operations of the pill dispensing device, a display in electronic communication with the memory, the processor, and the circuitry, and a pill pack incorporated within the housing of the pill dispensing device, wherein the pill pack includes a plurality of pharmaceutical pills.

According to other examples, a communication system of a pill dispensing device to facilitate communication with one or more sources is described. An example communication system may include an audiovisual component integrated within the pill dispensing device. The pill dispensing device may include an electronic ink display configured to provide a graphical user interface (GUI), and a microphone and one or more speakers. The communication system may also include a processor of the pill dispensing device configured to collect and store data associated with one or more of pill consumption and a user, and a server in electronic communication with the audiovisual component. The server is configured to notify the processor to display information to the user through the GUI and/or another computing device associated with the user, and provide at least a portion of user information received from the processor to a third party.

According to further examples, a pill consumption detection system integrated with a pill dispensing device is described. An example detection system may include a trace diagram comprised of one or more conductive ink traces printed on a pill pack configured to detect a modification to the pill pack, an electronic connection from the trace diagram to circuitry of the pill dispensing device, and a processor in electronic communication with the circuitry of the pill dispensing device configured to collect pill consumption information about a user.

According to yet further examples, a method of manufacturing a pill pack with an integrated detection system incorporated within a housing of a pill dispensing device is described. An example method may include creating a trace diagram, printing a printout of the trace diagram on a biodegradable substrate, and connecting the conductive printout of the trace diagram to at least one of: a backing of the pill pack integrated with the pill dispensing device and a circuitry of the pill dispensing device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
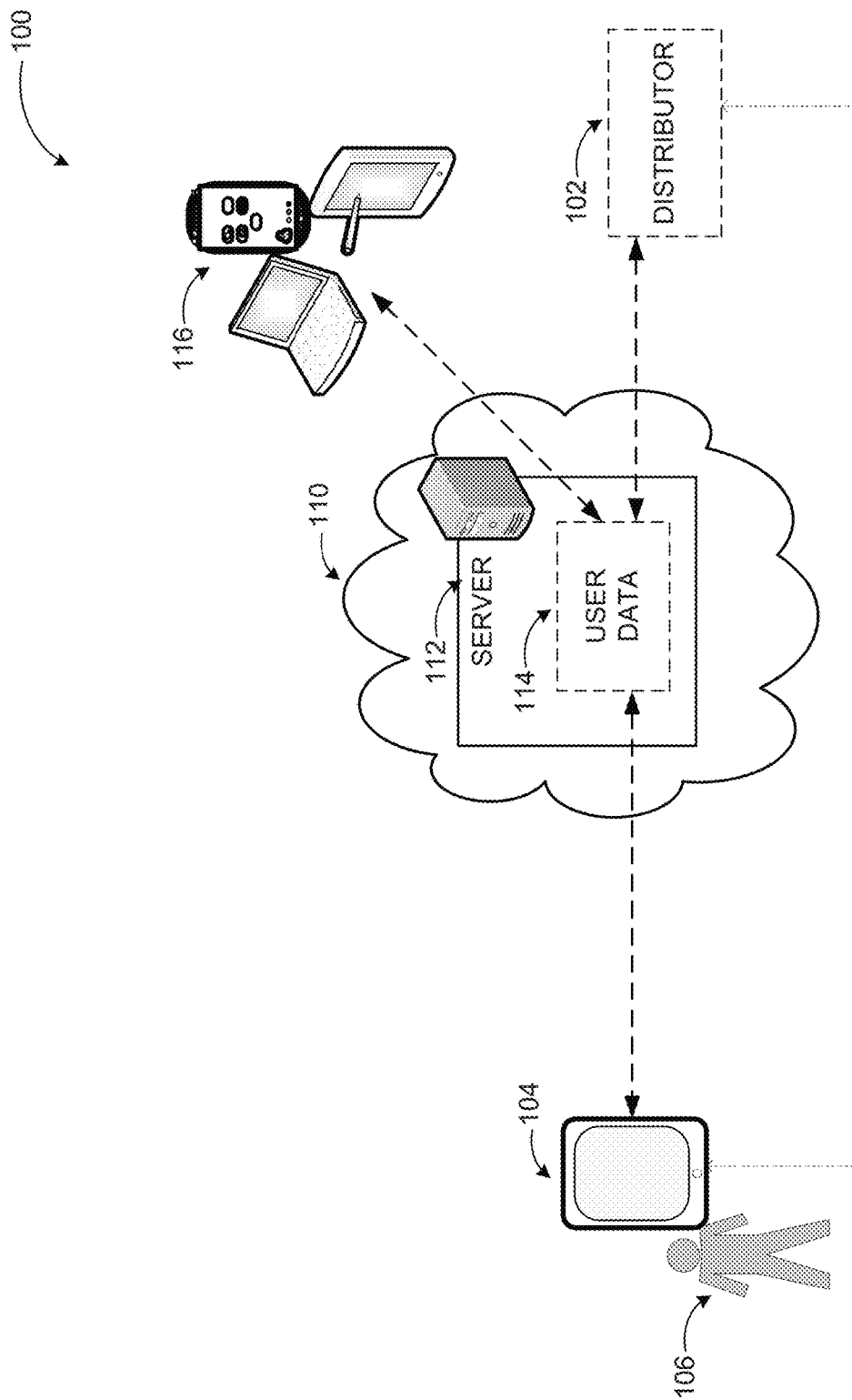
FIG. 1 illustrates an example system for providing a pill dispensing device to a user.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to providing an interactive adherence drug dispensing and communications platform.

Briefly stated, technologies are generally described for providing a pill dispensing device with adherence monitoring and alerting features, as well as communication capabilities. A pill pack may be integrated within a housing of the pill dispensing device, where removal of each pill in the pill pack may be monitored through a conductive trace or comparable mechanism. Timing of the removal, remaining pills, and similar information may also be detected by the pill dispensing device and provided along with additional information such as health status of the consumer monitored by one or more sensors to a health care provider or similar entity over wired and/or wireless networks. The pill dispensing device may include audio and/or visual output device(s) to provide alerts and health/medication related information to the consumer. A display technology may be employed enabling continuous display with low power usage such as ink display while providing color and/or video capabilities.

FIG. 1 illustrates an example system for providing a pill dispensing device to a user, arranged in accordance with at least some embodiments described herein.

As demonstrated in a diagram 100, a distributor 102 may provide a pill dispensing device 104 to a user 106. The pill dispensing device 104 may be customized for the user. The pill dispensing device 104 may include a pack of pills requested by the user, such as a monthly prescription. The pill dispensing device 104 may also be preprogrammed with user specific data and/or applications that the user may view and interact with on the device. For example, different monitoring or alerting applications may be provided depending on user (e.g., user may be disabled) or medication type. Content on the device may be updated subsequently via over the air (OTA) updates in response to changes at the distributor. The distributor may monitor the pill consumption by the user by tracking each pill within the pill dispensing device. Information about the pill consumption may be communicated to the distributor via OTA communication.

In an example embodiment, the user specific data, including demographic and/or biometric data about the user and data about the user's pill consumption may be stored in a data store 114 on a server 112. The server 112 may be hosted on a network associated with the service provider, and in another embodiment, the server may be hosted in a cloud network 110. When the user receives the pill dispensing device 104, the device may include an initial set of data, which may be user specific data provided by the distributor, and may also include default presets related to the pill consumption. For example, the pill dispensing device 104 may include preprogrammed alerts for notifying the user when it is time to take a pill. The preprogrammed alerts may be a default time based on the pill instructions, and additionally may be preprogrammed based on observed and/or learned user preferences. The distributor 102 may also be able to provide additional data to the device via communication with the device over the network. The device may be configured to communicate with the service provider over the network via wireless communication. Example wireless communication may include cellular communication, local area or wide area network (LAN or WAN) communication, optical communication, and/or near field communication (e.g., Bluetooth) with another device which may communicate with the distributor over the network. The device may also communicate over the Internet via wireless communication. In some embodiments, the user may provide input on the device, and the input information may be provided to the distributor over the network via one or more of the described communication methods.

The server 112 may be configured to maintain a database of user profiles, and the server may manage the user profiles and the deployed devices to users. The server 112 may also export user data to third parties. The server may also provide a dashboard that users may access to control the user profile. The dashboard and the user data may be accessible on other devices 116 such as a personal computer, PDA, cellular telephone, tablet etc. The server 112 may also be configured to enable access to other medical records databases and to maintain the data such that the data may be compatible with other medical records and data stores online.

In another example embodiment, the distributor 102 may track the pill dispensing device to monitor when the user receives the device, and also to monitor for tampering with the device before the user receives the device. Additionally, the device may be tracked to determine when the user is finished with the device and disposed of the device or returns the device to the distributor for recycling. The device may be tagged with an RFID tag, a QR code, a bar code, or other similar tagging mechanism for tracking the device over its life cycle.

In yet another example embodiment, the device may include biometric identification and monitoring for security purposes, identification for multiple users of the device, and for tethering the device to additional health monitoring devices. For example, the device may be tethered to a health monitoring device such as a blood pressure device or oxygen device that contains data associated with the user. The device may be configured to gather the health data from the health monitoring devices, and include the data in the user profile associated with the pill dispensing device for generating a complete health profile of the user. In another example, multiple users, such as a husband and wife, may utilize a single pill dispensing device, and the pill dispensing device may be configured to identify which user is removing a pill from the device employing biometric identification techniques in order to track that the user is taking the correct pill. The pill dispensing device may also include additional security features for securing against children. A security feature may be a manual lock and may also include a touch screen interaction, by inputting a code, pattern, password, or other similar security technique. Other security techniques may also be employed for verifying the identity of the user and increasing security, including password, identification number, and other user credential verification to ensure security of user data if the device is lost, misplaced, or stolen.

In further examples, the device may include a geo-aware function. For example, the device may be equipped with location based technologies including, but not limited to Global Positioning Service (GPS), network based location determination, etc. The device may further include an accelerometer and/or a thermometer for environmental and/or usage monitoring. The device may also include computational and circuitry components, such as a memory, data storage, ARM CPU, and a GSM modem.

Figure 2:
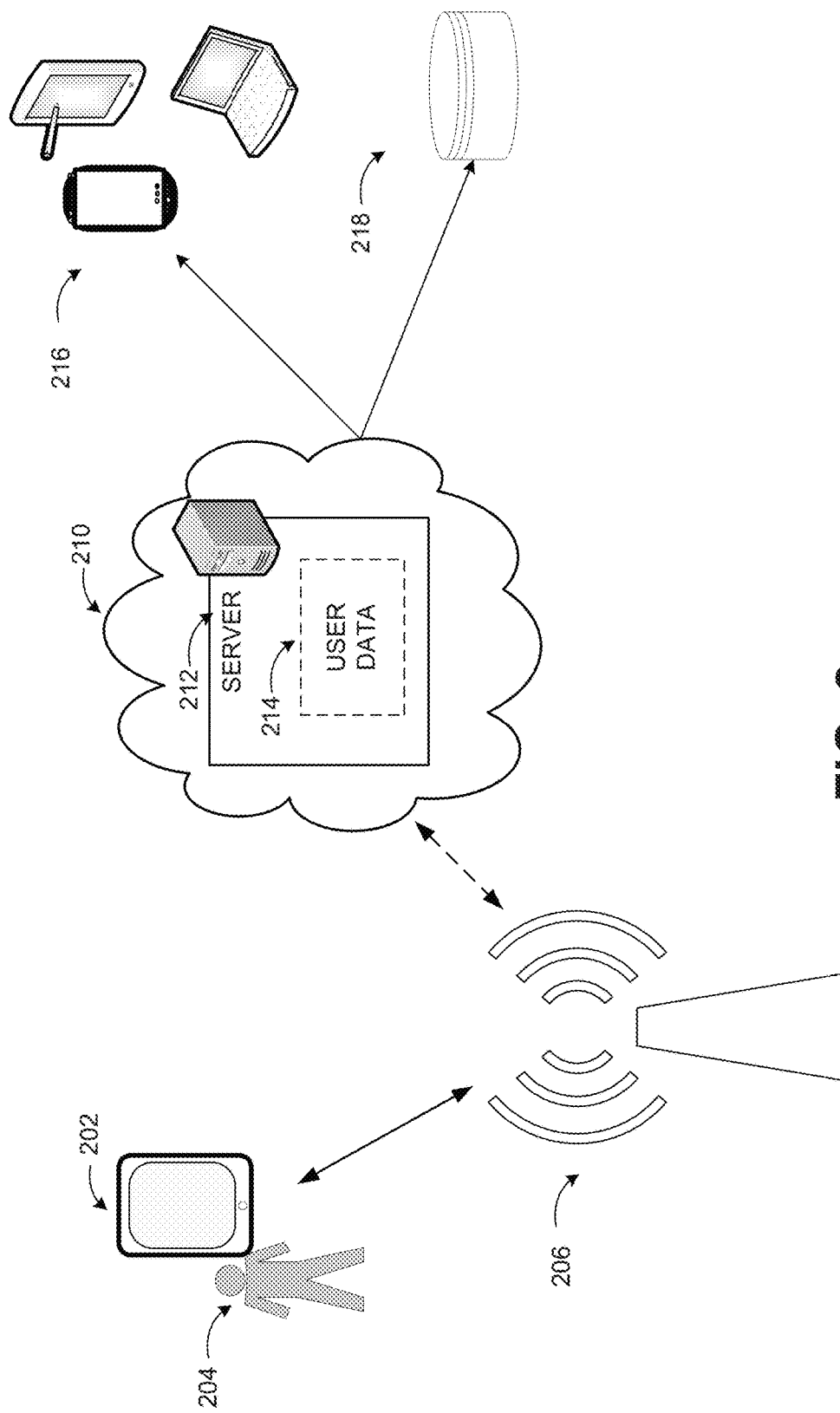
FIG. 2 illustrates an example server infrastructure and user interface configuration.

FIG. 2 illustrates an example server infrastructure and user interface configuration, arranged in accordance with at least some embodiments described herein.

As previously discussed in conjunction with FIG. 1, the pill tracking device 202 may be configured to communicate over a network such as a cloud network 210 via wireless communication, such as cellular communication 206. The cloud network 210 may host a server 212 via which the pill tracking device 202 may communicate with other devices 216, including but not limited to mobile devices, cellular phones, tablets, PDAs, in home displays (such as televisions, monitors), and personal computers. Additionally, the server 212 may enable the pill tracking device to communicate over the network with databases 218 such as medical databases and user profile databases for providing user data and pill tracking data to the databases and for retrieving data from the databases. Information associated with the pill tracking device 202 may be viewable over web browsing applications and email, as well, for enabling a user to access, view, and interact with data associated with the pill tracking device.

In addition, the server 212 may store pill tracking data to provide services associated with surveys and questionnaires in relation to the pill tracking data. The server 212 may allow integration of pill tracking data with surveys or questionnaires provided from external resources. The server 212 may transmit the surveys or questionnaires to the pill tracking device 202 to be populated by the user 204. The server 212 may receive completed surveys or questionnaires from the pill tracking device 202. The completed surveys or questionnaires may be transmitted to the external resources.

The server 212 may anonymize the surveys or questionnaire or the completed surveys or questionnaires to remove patient identifier information. Alternatively, the server 212 may provide survey or questionnaire building tools to enable external parties to build surveys or questionnaires for the pill tracking device 202. Data associated with the completed surveys and questionnaires may be integrated with pill tracking data and provided for data mining. Furthermore, the server 212 may adjust surveys and questionnaires dynamically based on pill tracking data to target the surveys or questionnaires to specific attributes associated with the user 204 such as pill consumption information.

The server 212 may also anonymize the user data 214 to remove user identifying information associated with pill tracking data. The server 212 may provide data sharing services to share the pill tracking data with external parties. The data sharing services may be configured based on privacy rules limiting exposure of the pill tracking data. Exposure of the pill tracking data may be limited based on privileges associated with external parties requesting access to the pill tracking data. The data sharing services may provide access to pill consumption adherence or usage information associated with the pill tracking data to external parties.

Furthermore, the server 212 may transmit customized messaging to the user 204. The customized messaging may include advertisements and education. The server 212 may provide access to the pill tracking data to allow external parties to customize the messaging to target attributes associated with the user 204. An example may include a training pamphlet associated with importance of taking pills on time as a customized message. The message may have been customized with pill tracking data indicating missed usage.

Figure 3:
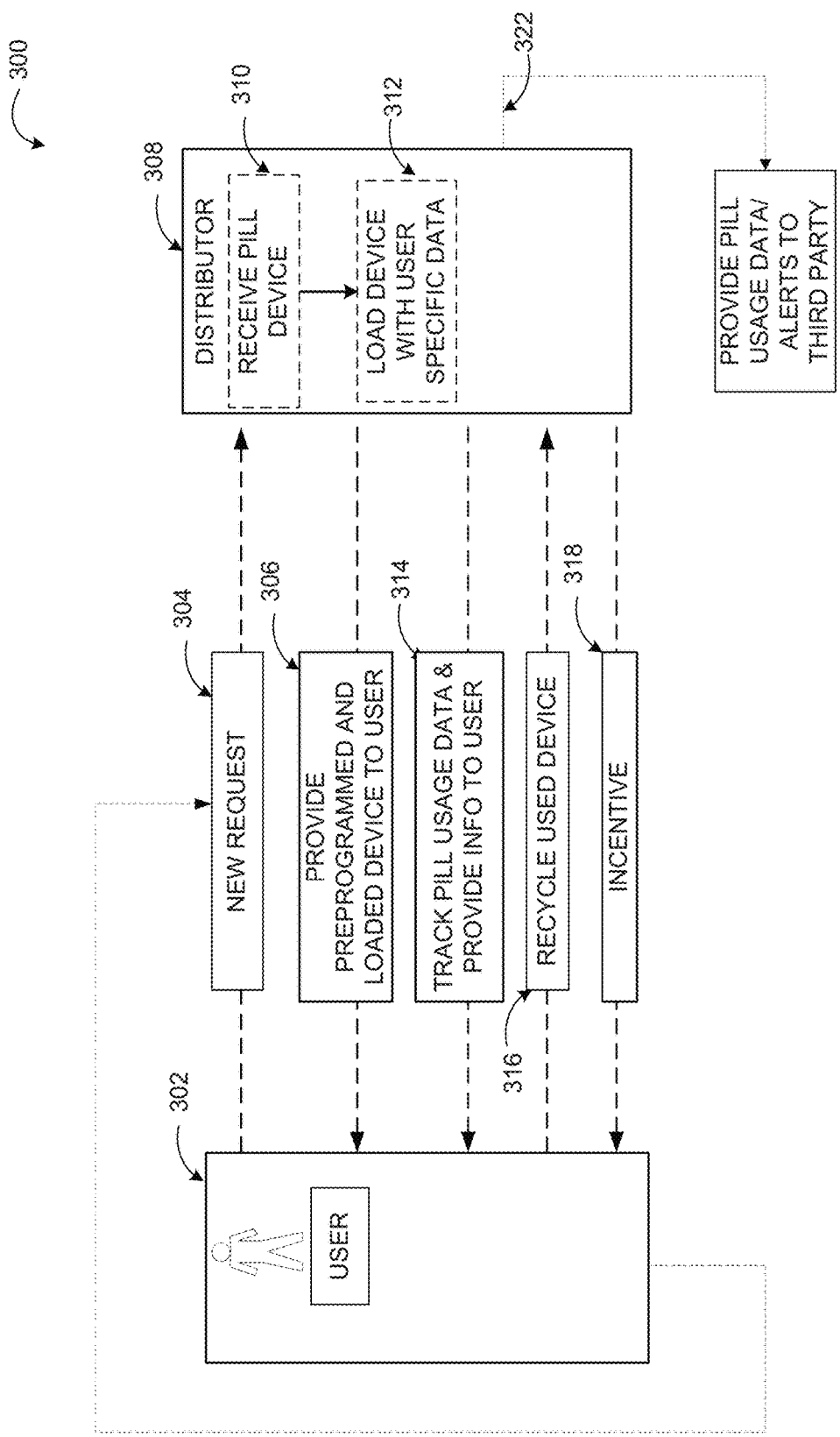
FIG. 3 illustrates an example scenario of interactions between a user and a distributor providing a pill dispensing device.

FIG. 3 illustrates an example scenario of interactions between a user and a distributor providing a pill dispensing device, arranged in accordance with at least some embodiments described herein.

As illustrated in diagram 300, a user 302 may request 304 a pill dispensing device from a seller or supplier 308, such as a pharmaceutical company or pharmaceutical distributor, a hospital, a doctor's office, an online retailer, or other supplier, for example. The seller or supplier 308 may manufacture, or receive 310 from a manufacturer, the pill dispensing device and load 312 the prescription pill pack into the housing, including conductive traces for tracking each pill. The seller or supplier 308 may also preprogram the computational components with user specific data. The seller or supplier 308 may provide 306 the device to the user with the prescription pill pack and preprogrammed features, such as a notification application, calendar application, and other similar data and applications customized for the user. For example, the preprogrammed data may include alerts and notifications related to the timing and dosage of pill consumption and information about the pharmaceuticals, including standard label information such as ingredients, warnings, side effects, directions, storage, symptoms, and other drug related information.

The pill dispensing device loaded with the pill pack of prepackaged pills, and the user specific data may be provided to the user. The user 302 may interact with the pill dispensing device to extract a pill for taking, and also to view notifications and information provided on the device. Additionally, the data on the device may be updated by the seller or supplier 308 as the data changes over time, new information is received, and when the seller or supplier desires to provide additional messages and alerts to the user.

In an example embodiment, the pill dispensing device may be configured to track 314 when a pill is consumed by the user, to alert the user when it is time to take a pill, and to notify a third party 322 if the user does or does not take the appropriate pill at the right time. The pill dispensing device may provide specific information about which pill to take, or a dosage amount required. The pill dispensing device may be configured to track 314 each pill in the pill pack in order to confirm that the user indeed takes the correct pill. The pill dispensing device may provide a reminder alert if the user misses a scheduled pill. Additionally, the pill dispensing device may notify a third party 322, such as a caregiver, physician, pharmaceutical company, pharmacist, emergency party, family member and the like if the user misses a scheduled pill, and/or takes the wrong dosage.

In an example embodiment, the pill dispensing device may be programmed to schedule an alert for the user to take a pill at a scheduled time. In an example scenario, the pill dispensing device may initially enable the user to take pills at any time the user pleases. The pill dispensing device may observe the user's behavior and habits for when the user prefers to take the pills over an initial period of time, such as a week, and the pill dispensing device may automatically program alerts around the observed user behavior after a certain amount of time. The user's observed pill taking behavior may be saved to the user profile data which the seller or supplier may access. Subsequent pill dispensing devices used by the user may be provided to the user with preprogrammed alerts corresponding to the learned user behavior such that subsequent pill dispensing devices need not engage in an initial user behavior analysis to schedule alerts. Additionally, the user may customize the time and type of alerts on the pill dispensing device to specify when the user would like to receive the alert. For example, the user may interact with the interface of the pill dispensing device to schedule alerts and reminders. The pill dispensing device may include a calendar application for enabling the user to easily schedule the alerts. The user may also customize the type of alerts, including visual, audio, and/or vibration, as well as configure the alerts to be sent to other devices, such as the user's cellular telephone, PDA, tablet, or other computing device. Further, the pill dispensing device may provide a reminder to the user to re-order a new pill dispensing device when the current pill pack is almost empty and/or expired. The pill dispensing device also may automatically alert the seller/supplier, pharmacy, and/or pharmaceutical company when the pill pack is almost empty such that a new pill dispensing device may be provided to the user before the user takes the last pill so that the user does not miss a day.

In some example embodiments, at the end of the life of the device, the user may discard the device. The device housing and the computational components within the device may be composed of a material such that the device may be refurbished and reused. Alternatively, the materials may enable biodegradation based recycling of the device. The seller or supplier 308 may provide incentive(s) 318 to the user to return the used device to the seller or supplier or recycle 316 properly.

In an example embodiment, the housing, or packaging, may be composed of a biodegradable and/or decomposable material, such that the user may recycle the device when finished using it. Some example materials for manufacturing the device housing may include cellulose based materials, plastics, polymers, starch-based materials, wood or other plant based fiber products, paper products and other similar biodegradable materials. The above listed example materials may enable the user to discard the used device as waste, and the device may decompose naturally. Additionally, the above listed materials may enable the device to be recycled at a recycling facility where portions of the device may be recycled and reused. Further, the device may be returned to the seller or supplier where the pill dispensing device may be refurbished and reused by subsequent users to prevent waste and to prevent costs of manufacturing pill dispensing devices from scratch. Alternatively, the seller or supplier may be allowed to reprogram logic of the pill dispensing device to dispense a new drug with a new dosage and replace the pill pack for continued use of the pill dispensing device.

In another example embodiment, a manufacturer may integrate patient protection and security features into the device. The device may be allowed to record events such as removal of a component including the pill pack, the housing, the packaging, and similar ones. The device may be allowed to record an excess temperature, an excess humidity, a drop, and similar physical environmental attributes. The recorded events may be transmitted to external parties. Rules associated with disabling the device may be triggered based on logic evaluating the recorded events as unsafe triggers associated with the use of the device. Furthermore, an alert may be displayed on the device to inform a user about the recorded events.

In another embodiment, some components within the device may be composed of biodegradable and/or decomposable components to avoid waste and health hazards associated with improper disposal of the device. Such components may include the housing, circuit board(s), and other structural components. Some example materials utilized for manufacturing biodegradable and decomposable components may include biodegradable polymers, starch-based materials, wood or other plant based fiber products, paper products and other similar biodegradable materials.

Further, the device may enable the personal information and data stored on the device to be destroyed upon a trigger event, disposal, recycling, and/or refurbishment of the device after use. In an example embodiment, the device may include a trigger device for activating (or releasing) a signal to accelerate the biodegradation of the biodegradable components. Example signals may include a compound, chemical agent, and/or electrical signal. A trigger may include a button, a pull tab, or other similar action item included on the device. Additionally, the trigger may be activated remotely via communication with the device. Remote trigger may be especially useful in the case of a lost or displaced device. The remote trigger may instigate the device to erase its memory and a presently displayed image.

Figure 4:
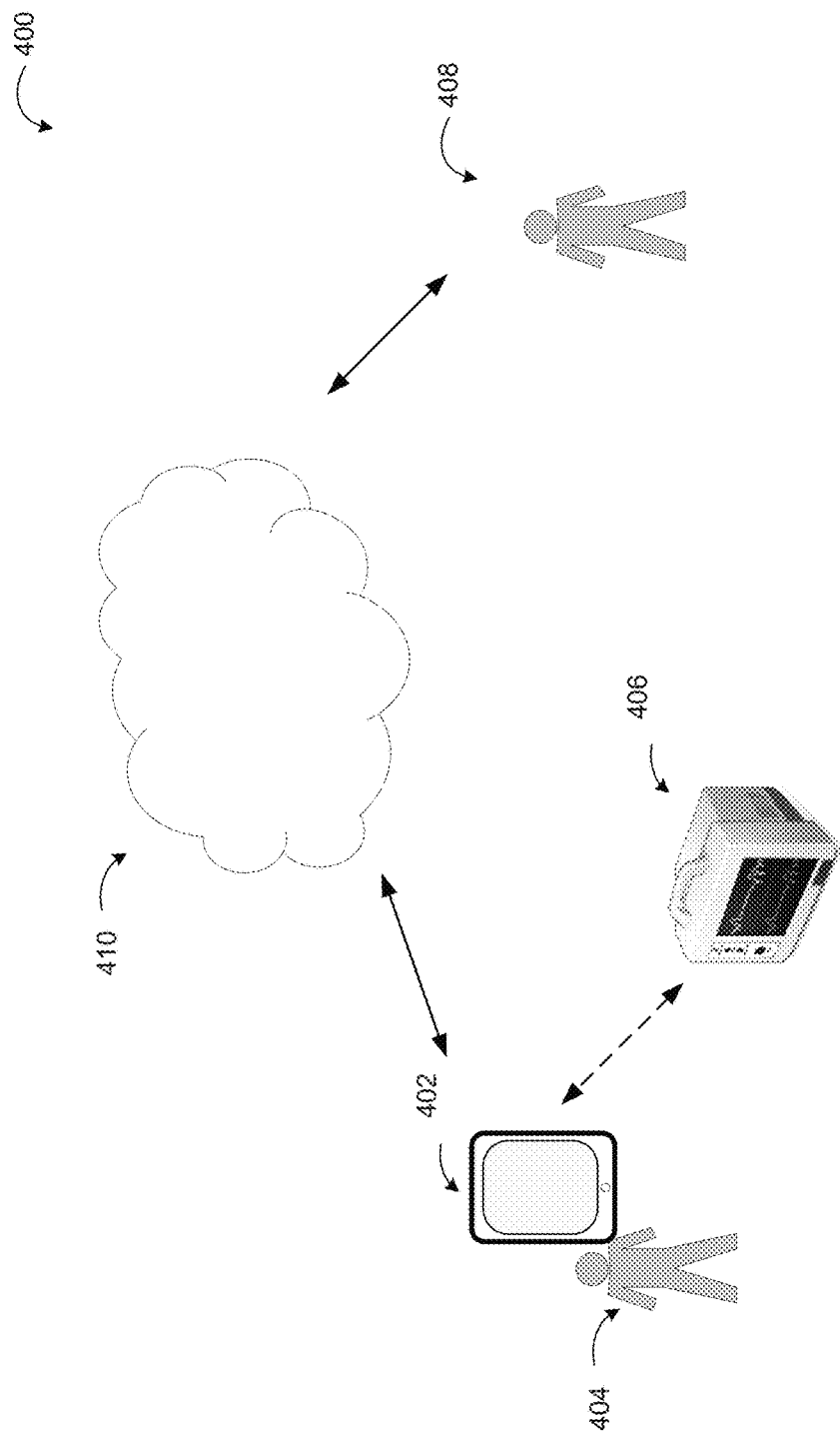
FIG. 4 illustrates an example schematic of exchanged communication employing a pill tracking device.

FIG. 4 illustrates an example schematic of exchanged communication employing a pill tracking device, arranged in accordance with at least some embodiments described herein.

As illustrated in diagram 400, two-way communication may be enabled between the pill dispensing device 402 and a third party 408. As discussed above in conjunction with FIG. 3, the pill dispensing device may be configured to alert the user 404 when it is time to take a pill. The pill dispensing device 402 may provide specific information about which pill to take, or a dosage amount required, and may also provide a reminder alert if the user misses a scheduled pill. Additionally, the pill dispensing device may notify a third party 408, such as a caregiver, physician, pharmaceutical company, pharmacist, family member and the like if the user misses a scheduled pill, and/or takes the wrong dosage. The pill dispensing device may also enable the third party 408 to send messages to the user over the pill tracking device for providing information and asking questions in order to receive direct feedback from the user about side effects and symptoms, and other health related issues. The pill tracking device may provide compliance information, such as if and when the user fails to take a pill, to the third party 408. Further, the pill dispensing device may connect with other health monitoring devices 406 to retrieve health information about the user, and the pill dispensing device may also provide the retrieved health information to the third party 408 over the network. As previously described, the communication may be facilitated over a network, such as a cloud network 410 or other wireless communication.

Figure 5A:
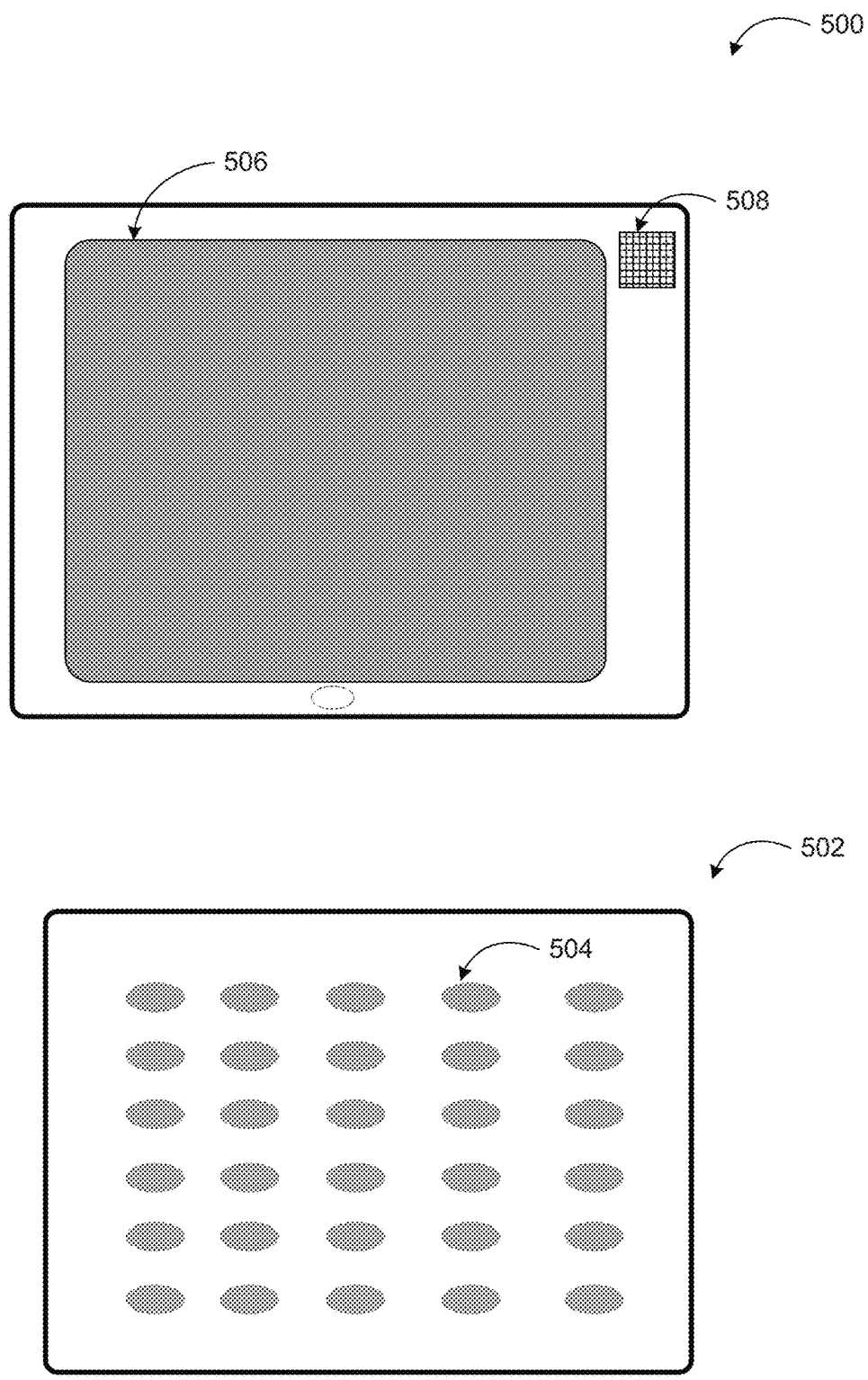
FIGS. 5A and 5B illustrate an example pill dispensing device.
Figure 5B:
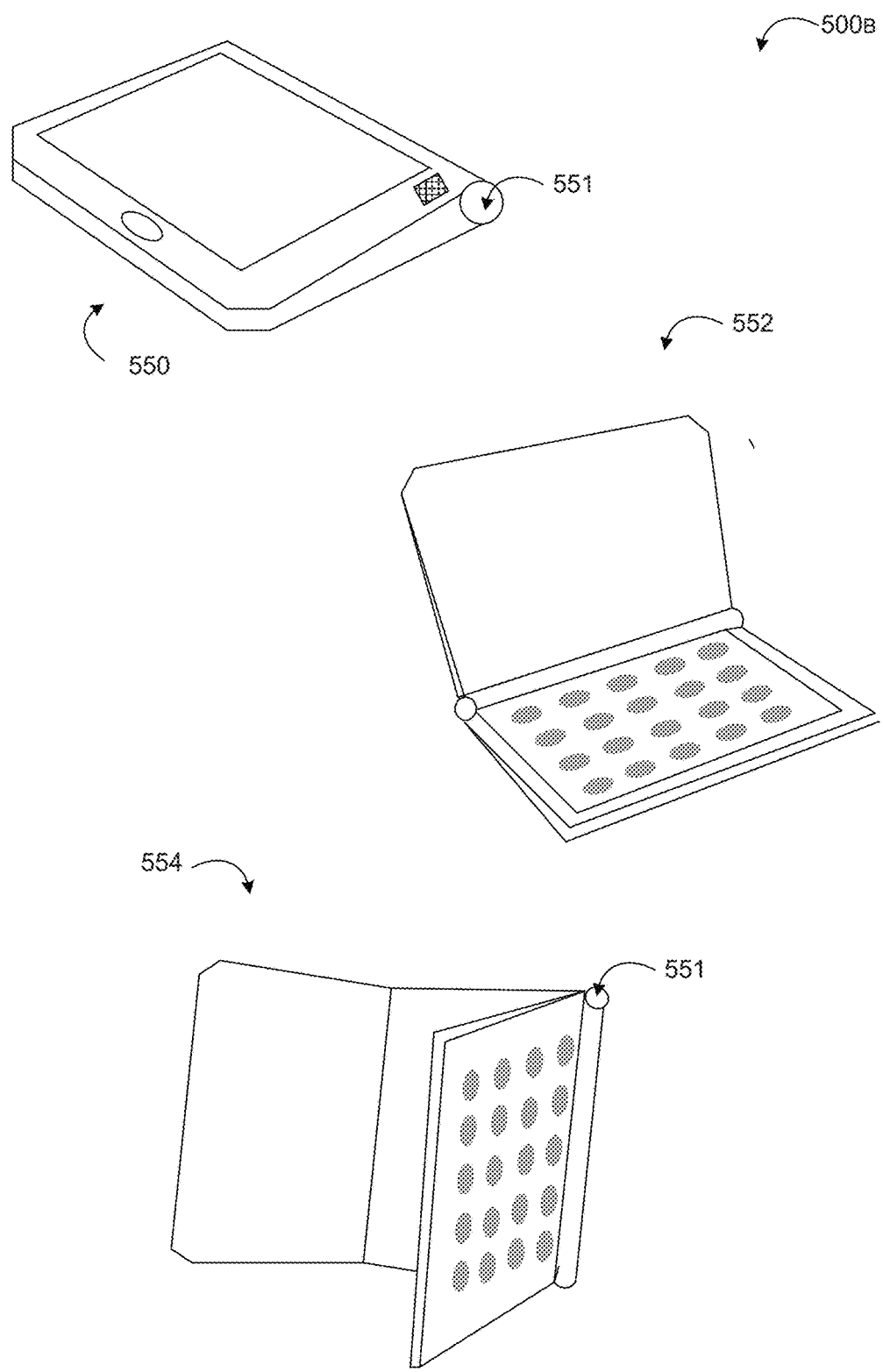

FIGS. 5A and 5B illustrate an example pill dispensing device, arranged in accordance with at least some embodiments described herein.

As illustrated in diagram 500A, and as described above, the pill dispensing device may be loaded with one or more prescription pill packs. The pill pack 502 may be a blister or bubble pack such that each pill 504 is enclosed in a cavity or pocket in the pill pack which may be composed from a thermoformed plastic. The pill pack 502 may include a paper, plastic, and/or foil backing, and each pill may be popped out through the backing with a minimal push force by the user. Each pill in the pill pack may be tracked such that the device can determine if and when a user takes a pill and exactly which pill is taken.

Additionally, as illustrated in diagram 500, the device may include a graphical user interface (GUI) 506 such as an electronic ink display with video capability using grayscale or color for enabling the user to interact with the device for viewing information and also for providing input to the device. The GUI may be configured to be constantly on employing low power technology such as electronic ink and long term batteries. The GUI may be a touch screen interface, and may enable traditional input methods such as pen, keyboard, and mouse. The touch screen interface may be a capacitive touch screen, and/or an IR and resistive touch panel also. The GUI may be an electronic ink display as will be described in further detail below. The device may also include a microphone 508 and one or more speakers to facilitate communication.

In some example embodiments, as illustrated in diagram 500B, the device 550 may resemble a clamshell, such that the device generally includes two halves joined by a hinge 551 which allows the device to come together to close. In the example embodiment 552, one half of the housing may include the pill pack, and the other half may include the GUI for enabling the user to interact with the device. Additionally, multiple pill packs may be incorporated with the device. Example embodiment 554 show how each pill pack may be inserted as a page within the device and may be attached at the hinge 551. Additional pill packs may also be attached to the edge of other pill packs such that the pill packs may fold onto each other, interlock with each other, and fit within the interior of the device to reduce a physical size and profile of the device. The pills may be removed from the pill pack by opening the device to reveal the pills on the interior of the device. Alternatively, the pills may be removed from the backside of the device. In another example embodiment, the pills may be automatically dispensed from the pill pack at the appropriate determined time for the user to take the pill. Times associated with dispensed pills and missed pills may be tracked by the device. The device may provide an adherence report based on the times associated with dispensed pills and missed pills. The adherence report may be transmitted to a server for data storage or to a third party in order to inform the third party about pill consumption adherence by the user.

In an example embodiment, the housing of the device may be composed from biodegradable materials, such as biodegradable and/or decomposable material including but not limited to plastics, polymers, starch-based materials, wood or other plant based fiber products, paper products and other similar biodegradable materials as described above. The structure of the housing may be manufactured to enable stacking of multiple devices with a low profile. The pill pack may be incorporated with the housing such that the pill pack becomes a part of the device and is not removable by the user. In another embodiment, the pill pack may be removable and replaceable by the user so that the user can install a refill pill pack rather than receiving an entirely new pill dispensing device. Holes may be formed in the housing to match the layout of the pills within the pill pack.

Figure 6:
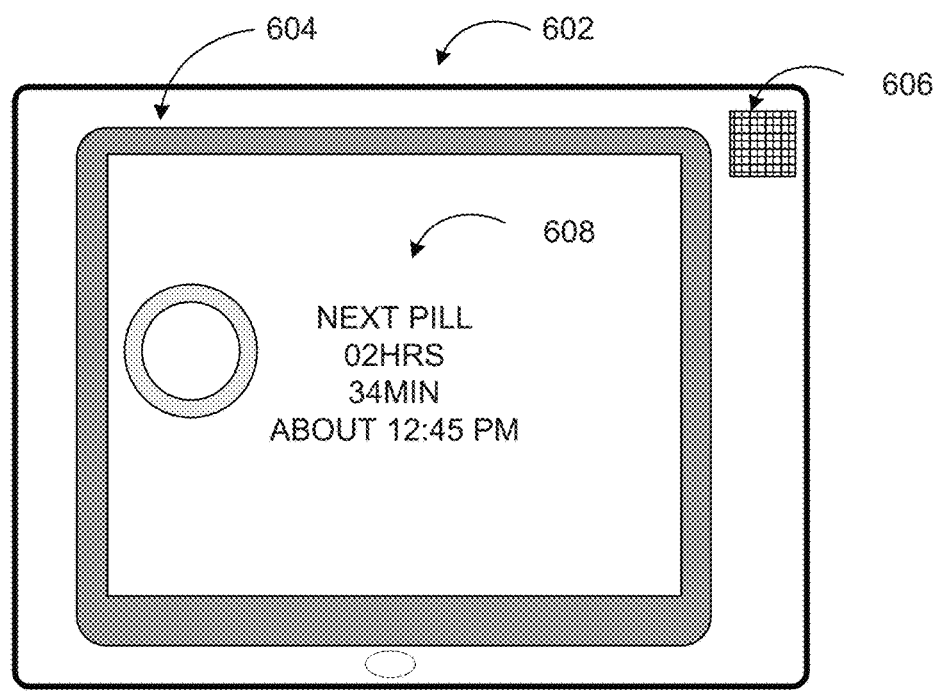
FIG. 6 illustrates example configurations of a graphical user interface (GUI) of a pill dispensing device.

FIG. 6 illustrates an example configuration of a graphical user interface of a pill dispensing device, arranged in accordance with at least some embodiments described herein.

As previously discussed, the device 602 may include a graphical user interface (GUI) 604 for displaying information 608 and enabling a user to interact with the device. The GUI 604 may display messages, calendars, alerts, charts, and other information for the user. The information provided may include visual, audio, and tactile notifications, wherein a vibrating feature and an LED light feature enable the visual and tactile notifications. The user may also interact with the GUI employing touch input and other input methods.

The device may include a combined microphone and speaker 606 for enabling audio interaction and communication. Two way communication may be enabled for the user to ask questions to the device, and the device may be configured to provide an answer to the question based on preprogrammed responses, searching for an answer in a database, or by transmitting the question to a third party and enabling the third party to provide an answer. Additionally, two way communication may enable a third party to pose questions to the user employing the device and for the user to respond to the question. Additionally, the GUI 604 may provide textual and graphical information, and may include calendars and charts for scheduling and tracking pill consumption. The GUI 604 may be configured to display a winning streak for indicating a continuous number of the days the user has taken the pills, and comparing cycles of pill taking for encouraging the user. The device may also include a security mechanism such as a mechanical locking feature and/or an electronic locking feature controlled via the GUI. The GUI 604 may provide a share button to allow a user to share patient information with a third party such as a doctor's office and similar ones. In addition, the GUI 604 may be configured to display a graphical inventory map of remaining or used pills. In addition, the GUI 604 may also be configured to retain a last image displayed by the pill dispensing device.

In some embodiments, the GUI 604 may be an electronic ink display. Electronic paper, e-paper and electronic ink are display technologies designed to mimic the appearance of ordinary ink on paper. Unlike conventional backlit flat panel displays which emit light, electronic paper displays reflect light like ordinary paper, making the display more comfortable to read under various lighting conditions. Their surfaces may, thereby, have a wider viewing angle than conventional displays. The contrast ratio of such displays may in some cases be better than real paper newspapers allowing them to be read in direct sunlight without the image appearing to fade. Some electronic paper technologies may hold static text and images indefinitely without using electricity. The display may be composed of a plastic or polymer substrate, for example, and may also be other materials including glass. The display may be touch enabled, and may be a resistive, capacitive, and/or optical touchscreen in some embodiments.

Figure 7:
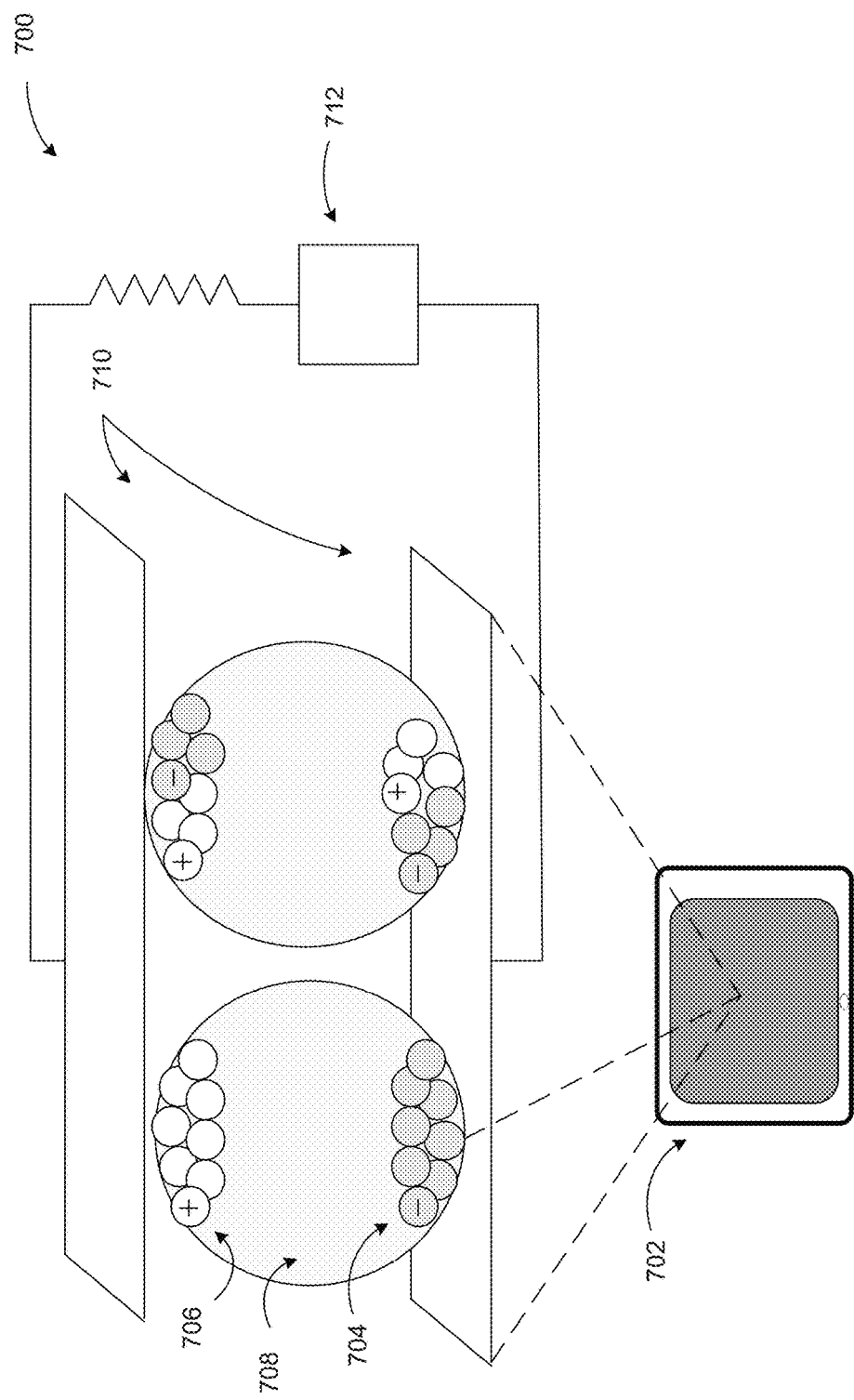
FIG. 7 illustrates an example configuration of an electronic ink display comprising a graphical user interface (GUI) of a pill dispensing device.

FIG. 7 illustrates an example configuration of an electronic ink display comprising a graphical user interface (GUI) of a pill dispensing device, arranged in accordance with at least some embodiments described herein. As discussed previously in FIG. 6, the pill dispensing device may include a graphical user interface 702, which may be an electronic ink display, for displaying information and enabling a user to interact with the device. As illustrated in a diagram 700, on some electronic ink displays, the electronic ink may be composed of charged particles 704 and 706 dispersed in a liquid 708, such as oil, that may be deposited on the back side of the display. The electronic ink mixture, including the charged particles 704 and 706 dispersed in the liquid 708 may be placed between two parallel conductive plates 710 separated by a small distance, and deposited on the back side of the display.

A voltage 712 may be applied across the plates 710 to cause the charged particles to polarize, or flip states. When the charged particles polarize, they may become located proximal to the viewing side of the display. When the particles are located near the viewing side of the display, the display may appear light and when the particles are located away from the display, the display may appear dark. The conductive plates may be divided into pixels such that the particles can be polarized on a pixel by pixel basis to form text and images on the display.

The ink display of the device may also enable video capabilities employing dithering techniques, as well as a pixel-toggling technique in which a video may be displayed at a lower resolution than the display resolution and the video may be slightly moved around portions or quadrants of the display incrementally over time. The device may also be equipped with a microphone and speaker for enabling audio features. LEDs (including a blinking light feature) and a vibrating feature may be integrated for providing visual and tactile notifications, respectively. In addition to keyboard and mouse input mechanisms (e.g., through NFC communications such as Bluetooth), modem interaction technologies such as touch, optically captured gesture, eye-tracking, input pen, gyroscopic input, etc. may also be enabled.

One of the features of electronic ink displays is that steady display state is non-parasitic. That is, unlike conventional LCD or similar displays, which require electrical power to display any image (static or moving), electronic ink displays need power only to change their state. Thus, useful information on the entire display, or parts of the display, may be retained without drawing power from the battery. While conventional electronic ink displays update pixels for an entire displayed page in response to a change in even a small portion of the displayed page, a display according to several embodiments may change or refresh only pixels that need to be changed as opposed to the entire displayed page further preserving energy.

An electronic ink display is bistable, and as a result, the display may be able to remain on at all times without needing much power. As the display is altered, portions of the electronic ink in the display may be polarized to flip the state on a pixel by pixel basis to generate text and images on the display. The power to flip the pixels is very low, allowing a battery to last a long time. Various battery technologies (disposable or rechargeable) may be employed. Some example battery technologies may include alkaline batteries, gel batteries, nickel-cadmium batteries, Lithium-Ion batteries, carbon-iron batteries, and so on. For example, low self-discharge batteries may extend usage life of a device according to embodiments. In some embodiments, the device may utilize solar cell based power generation to complement or replace the battery, where solar cells may be implemented using conductive ink based electronics and biodegradable substrate to ensure degradability of the cells.

According to some embodiments, computational components, along with the electronic ink display, may be placed on the back side of the display (e.g., etched on the back side of the LCD glass) reducing part and assembly cost. Lithography or similar techniques may be employed to accomplish the placement of parts on the display. Additionally, computational and circuit board components may be etched directly on both sides of the display to enable surface-mounting of power and computational components directly to the display panel. Some techniques for etching the computational and circuit board components may include deposition of indium tin oxide (ITO), and other similar techniques.

Figure 8:
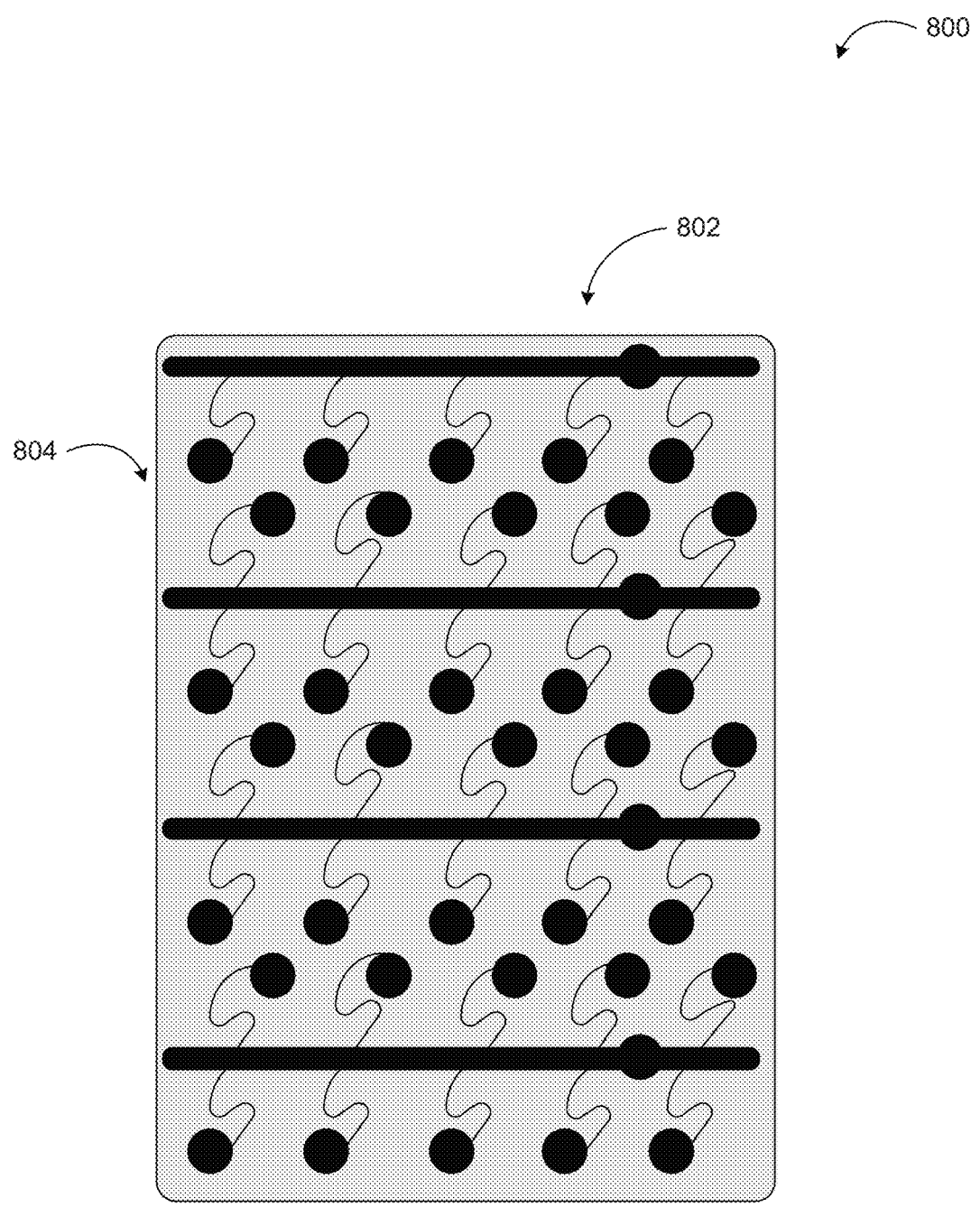
FIG. 8 illustrates example conductive traces on a pill dispensing device.

FIG. 8 illustrates an example pill pack including conductive traces, arranged in accordance with at least some embodiments described herein. As described above each pill in a pill pack incorporated within a pill dispensing device may be traced such that the device can track if and when a user takes a pill and exactly which pill is taken. In an example embodiment, each pill may be tagged or traced within the pill pack so that when the pill is removed from the pill pack, the device monitors exactly which pill is popped out. Some example tagging and tracking techniques may include RFID tagging, tracing the pill pack with conductive traces, and incorporating an IC circuit within the pill pack.

As shown in a diagram 800, a trace diagram 802 may be created to include a conductive ink 804 pattern matching a pattern of pills arranged within a pill pack, to allow each pill to be traced. A printout of the trace diagram may be printed to a 3D, inkjet printer using conductive ink.

In an example embodiment, conductive ink may be printed on a substrate, and the substrate may be attached to the pill pack. The printed conductive ink pattern may match the pattern of the pills within the pill pack such that each cavity containing a pill is traced. The conductive ink may be printed on the substrate employing ink jet printing technologies. In another embodiment, the conductive ink may be printed directly on the backing of the pill pack before the pill pack is assembled. The conductive ink may be layered between non-conductive layers such as a resin layer. The conductive ink may be configured to trace each pill by measuring a resistive change when a pill is removed from the pill pack. The conductive ink may also be configured to trace each pill by optical sensing and/or pressure sensing when a pill is removed from the pill pack. Other tracing techniques may be employed by including a tag on each pill and connecting each pill tag to a bridge. A magnet may be incorporated on the opposite side of the traces for maintaining the tags in place and resisting a spring effect. Additionally, conductive ink traces may be used to detect opening and closing of movable parts of the device (e.g., battery cover, device cover, memory or other connection ports, etc., for example) for anti-tampering and security monitoring as well as to keep track of usage.

Conductive ink technologies may be employed with the electronic circuitry to reduce the size and bulk of the device, as well as costs associated with manufacturing and recycling the device. Additionally, conductive ink technologies may enable use of biodegradable substrates along with application specific integrated circuits (ASICs) and similar integrated circuits for enabling recycling and refurbishing of the device. Conductive ink can withstand rigors of pressure, heat and moisture and may replace copper wire and bulky connections in circuits. Conductive ink circuits may be made from a range of conductive materials, and the conductive ink may be printed on substrates such as plastic, cloth and paper. Conductive ink may be printed on substrates employing ink jet printing technologies. In some examples, conductive ink may be deposited on the reverse side of the display component saving space and material.

Figure 9:
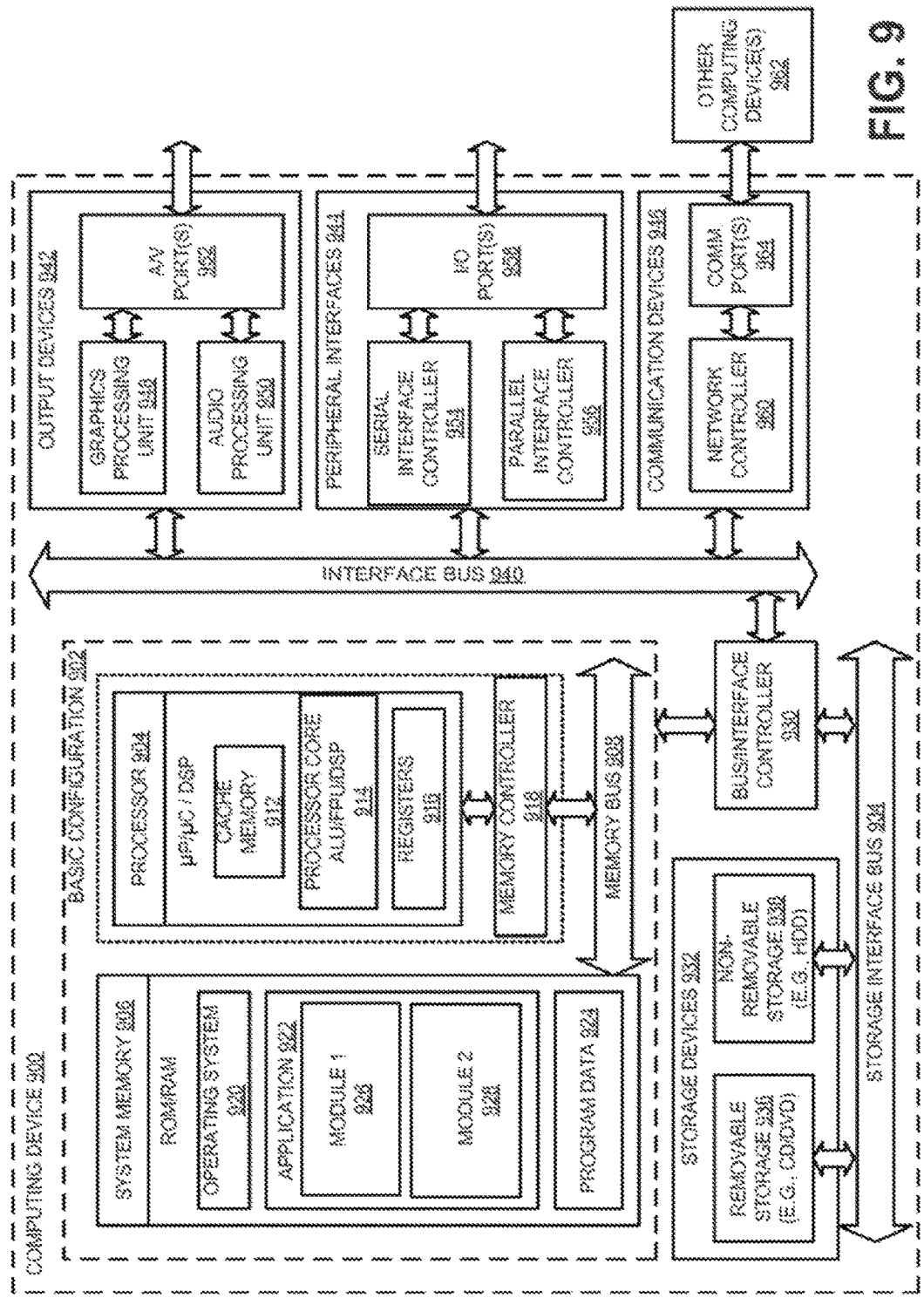
FIG. 9 illustrates a general purpose computing device, which may represent components and modules of a customized pill dispensing device.

FIG. 9 illustrates a general purpose computing device, which may represent a server for communicating with and monitoring a pill dispensing device, arranged in accordance with at least some embodiments described herein. In a very basic configuration 902, a computing device 900 typically includes one or more processors 904 and a system memory 906. A memory bus 908 may be used for communicating between a processor 904 and a system memory 906.

Depending on the desired configuration, the processor 904 may be of any type including but not limited to a microprocessor (µP), a microcontroller (µC), a digital signal processor (DSP), or any combination thereof. The processor 904 may include one or more levels of caching, such as a cache memory 912, a processor core 914, and one or more registers 916. An example processor core 914 may include an arithmetic logic unit (ALU), a floating point unit (FPU), a digital signal processing core (DSP core), or any combination thereof. An example memory controller 918 may also be used with the processor 904, or in some implementations, the memory controller 918 may be an internal part of the processor 904. The processor may possess a static netlist configuration, or be re-programmable in the form of a Field Programmable Gate Array (FPGA) or equivalent controller. The processor may also be an Application Specific Integrated Circuit (ASIC).

Depending on the desired configuration, the system memory 906 may be of any type including but not limited to volatile memory (such as RAM), non-volatile memory (such as ROM, flash memory, etc.) or any combination thereof. The system memory 906 may include an operating system 920, one or more applications 922, and program data 924. The application 922 may include one or more modules 926 and 928 for performing custom tasks as specified by the seller or supplier. Program data 924 may include user data, pill tracking data, recycling data, and similar data. This described basic configuration 902 is illustrated in FIG. 9 by those components within the inner dashed line.

The computing device 900 may have additional features or functionality, and additional interfaces to facilitate communications between the basic configuration 902 and any required devices and interfaces. For example, a bus/interface controller 930 may be used to facilitate communications between the basic configuration 902 and one or more data storage devices 932 via a storage interface bus 934. The data storage devices 932 may be removable storage devices 936, non-removable storage devices 938, or a combination thereof. Examples of removable storage and non-removable storage devices include magnetic disk devices such as flexible disk drives and hard disk drives (HDDs), solid state drives (SSDs), to name a few. Example computer storage media may include volatile and non-volatile, removable and non-removable media implemented in any method or technology for storage of information, such as computer readable instructions, data structures, program modules, or other data.

The system memory 906, removable storage devices 936 and non-removable storage devices 938 are examples of computer storage media. Computer storage media includes, but is not limited to, RAM, ROM, EEPROM, flash memory or other memory technology, or any other medium which may be used to store the desired information and which may be accessed by the computing device 900. Any such computer storage media may be part of the computing device 900.

The computing device 900 may also include an interface bus 940 for facilitating communication from various interface devices (e.g., output devices 942, peripheral interfaces 944, and communication devices 946) to the basic configuration 902 via the bus/interface controller 930. Example output devices 942 include a graphics processing unit 948 and an audio processing unit 950, which may be configured to communicate to various external devices such as a display or speakers via one or more A/V ports 952. Example peripheral interfaces 944 include a serial interface controller 954 or a parallel interface controller 956, which may be configured to communicate with external devices such as input devices (e.g., keyboard, mouse, pen, voice input device, touch input device, etc.) or other peripheral devices (e.g., printer, scanner, etc.) via one or more I/O ports 958. An example communication device 946 includes a network controller 960, which may be arranged to facilitate communications with one or more other computing devices 962 over a network communication link via one or more communication ports 964.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wireless media such as acoustic, radio frequency (RF), microwave, infrared (IR) and other wireless media. The term computer readable media as used herein may include both storage media and communication media.

While computing device 900 is shown with a number of example components, modules, and connections, those are intended for illustration purposes and do not constitute a limitation on embodiments.

Example embodiments may also include methods for monitoring pill consumption through a communication and detection system within a pill dispensing device. These methods can be implemented in any number of ways, including the structures described herein. One such way is by machine operations, of devices of the type described in the present disclosure. Another optional way is for one or more of the individual operations of the methods to be performed in conjunction with one or more human operators performing some of the operations while other operations are performed by machines. These human operators need not be collocated with each other, but each can be only with a machine that performs a portion of the program. In other examples, the human interaction can be automated such as by pre-selected criteria that are machine automated.

Figure 10:
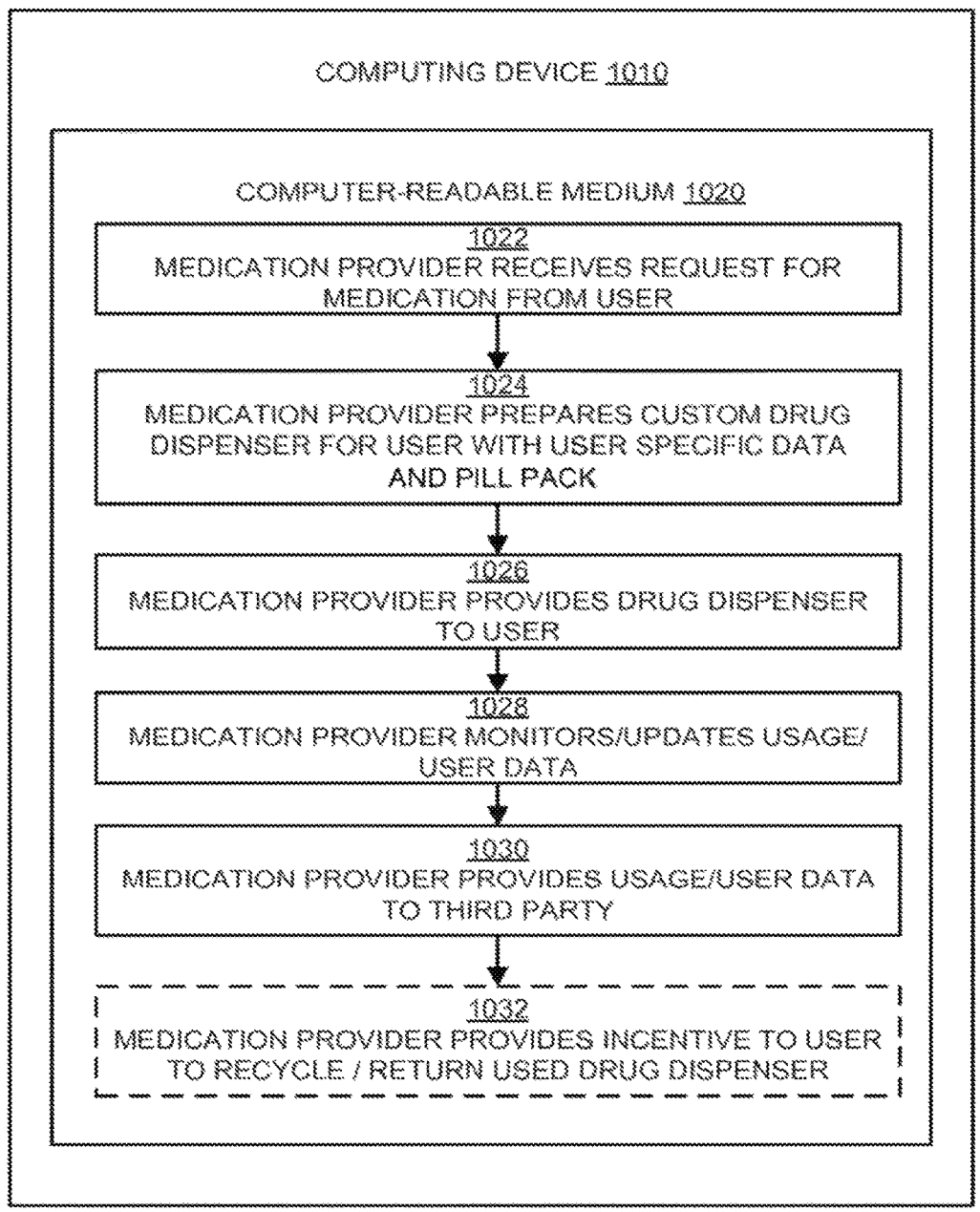
FIG. 10 is a flow diagram illustrating an example method that may be performed by a computing device such as the computing device in FIG. 9, all arranged in accordance with at least some embodiments described herein.

FIG. 10 is a flow diagram illustrating an example method that may be performed by a computing device such as the computing device in FIG. 9, arranged in accordance with at least some embodiments described herein.

Example methods may include one or more operations, functions or actions as illustrated by one or more of blocks 1022, 1024, 1026, 1028, 1030 and/or 1032. The operations described in blocks 1022 through 1032 may also be stored as computer-executable instructions in a computer-readable medium such as a computer-readable medium 1020 of a computing device 1010.

A process for providing a custom interactive pill dispensing device including user specific data may begin with block 1022, "MEDICATION PROVIDER RECEIVES REQUEST FOR MEDICATION FROM USER", where a medication provider may receive a request for medication from a user. The medication provider may determine user attributes, device characteristics, and pill packets associated with the user to customize a drug dispenser from a hardware, software, and pill pack perspective.

Block 1022 may be followed by block 1024, "MEDICATION PROVIDER PREPARES CUSTOM DRUG DISPENSER FOR USER WITH USER SPECIFIC DATA AND PILL PACK." At block 1024, hardware, software and product aspects of a drug dispenser may be customized. For example, custom specifications may be installed, user-specific data may be loaded, and depending on the user hardware features may be turned on/off, added, removed. The user's specific pill pack may be incorporated within the housing of the device and each pill may be traced.

Block 1024 may be followed by block 1026, "MEDICATION PROVIDER PROVIDES DRUG DISPENSER TO USER." At operation 1026, the device may be provided to the user. The device may be configured to have continuous network access and not to have to be turned off throughout its life in some example embodiments.

Block 1026 may be followed by block 1028, "MEDICATION PROVIDER MONITORS/UPDATES USAGE/USER DATA." At operation 1028, pill consumption may be tracked and monitored at the pill dispensing device. The pill dispensing device may provide reminders to the user to take pills, and may track when the user takes a pill. The pill dispensing device may also collect additional medical information and data about the user at the pill dispensing device, via input by the user and via communication with other health monitoring devices.

Block 1028 may be followed by block 1030, "MEDICATION PROVIDER PROVIDES USAGE/USER DATA TO THIRD PARTY." The monitored usage and user data may be provided to third parties. Usage and user data may include notifications pill consumption or failure to consume pills, and additional medical information and data about the user.

Block 1030 may be followed by block 1032, "MEDICATION PROVIDER PROVIDES INCENTIVE TO USER TO RECYCLE/RETURN USED DRUG DISPENSER." At optional operation 1032, the drug dispenser may be returned by the user to the medication provider for recycling or refurbishing. Alternatively, the user may be able to dispose of the device by simply dropping the device off at a recycling facility. A security feature such as a trigger may ensure protection of user data on the device. The medication provider may provide incentives to encourage the user to return the dispenser.

According to some embodiments, the pill dispensing device may be used as a direct mailer, in place of paper pamphlets, or other mailing materials associated with healthcare and pharmaceuticals. For similar or lower cost, an interactive Internet connected pill dispensing device may provide far more useful and engaging content to a prospective buyer of services/product(s) than paper based communication methods. Further, a device according to embodiments may be used as a communication device for gathering direct feedback from a user about issues, symptoms, and side effects associated with the pill consumption.

The blocks included in the above described process are for illustration purposes. Providing a pill dispensing device for monitoring pill consumption may be performed by similar processes with fewer or additional blocks. In some examples, the blocks may be performed in a different order. In some other examples, various blocks may be eliminated. In still other examples, various blocks may be divided into additional blocks, or combined together into fewer blocks. Although illustrated as sequentially ordered operations, in some implementations the various operations may be performed in a different order, or in some cases various operations may be performed at substantially the same time.

In some examples, a computer program product may include a signal bearing medium that may also include machine readable instructions that, when executed by, for example, a processor, may provide the functionality described above with respect to FIG. 9 and FIG. 10. Thus, for example, referring to the processor 904 one or more of the tasks shown in FIG. 10 may be undertaken in response to the instructions conveyed to the processor 904 by the signal bearing medium to perform actions associated with providing an interactive pill dispensing device including user specific data as described herein.

In some implementations, the signal bearing medium may encompass a computer-readable medium, such as, but not limited to, a hard disk drive (HDD), memory, etc. In some implementations, the signal bearing medium may encompass a recordable medium, such as, but not limited to, memory, etc. In some implementations, the signal bearing medium may encompass a communications medium, such as, but not limited to, a digital and/or an analog communication medium (e.g., a wireless communication link, etc.). Thus, for example, the program product may be conveyed to one or more modules of the processor 904 by an RF signal bearing medium, where the signal bearing medium is conveyed by a wireless communications medium (e.g., a wireless communications medium conforming to the IEEE 802.11 standard).

According to some embodiments, a pill dispensing device is provided including a housing, a memory adapted to store instructions, a processor adapted to execute the instructions stored on the memory, a communication module configured to facilitate communication with one or more sources for exchanging pill consumption and user data, a printed circuit board configured to support one or more of the memory, the processor, and circuitry associated with operations of the pill dispensing device, a display in electronic communication with the memory, the processor, and the circuitry, and a pill pack incorporated within the housing of the pill dispensing device, wherein the pill pack includes a plurality of pharmaceutical pills.

According to other examples, one or more of the memory, the processor, the circuit board, the display, and the housing of the pill dispensing device may include a biodegradable compound selected from: plastics, polymers, starch-based materials, wood, plant based fiber products, or paper products, and wherein a common feature of the compound includes being compostable. The pill dispensing device may further include a battery selected from one or more of: alkaline batteries, gel batteries, nickel-cadmium batteries, Lithium-Ion batteries, or carbon-iron batteries. In addition, the pill dispensing device may further include a trigger device configured to activate a signal to destroy user data stored on the pill dispensing device and/or to accelerate biodegradation of the pill dispensing device. The signal may be one or more of: a compound, a chemical agent, and an electrical signal. Alternatively, the trigger device may be configured to be mechanically activated or remotely activated.

According to further examples, the communication module of the pill dispensing device may be configured to communicate with a server over a network employing one or more of a cellular wireless communication, an optical communication, a near field communication, a wireless local area network communication, and a wide area network communication. The processor of the pill dispensing device may be preprogrammed by a seller or supplier with one or more of user specific data and a customized notification application. The display of the pill dispensing device may be configured to present one or more of an alert to remind the user to consume a pill, an instruction associated with the pill, and information received from a third party. The pill dispensing device may be configured to collect pill consumption information about the user. The pill dispensing device may be configured to collect medical information about the user via input by the user. Alternatively, the pill dispensing device may be configured to collect medical information about the user via communication with one or more health monitoring devices. In addition, the pill dispensing device may further include one or more of an RFID tag, a QR code, and a bar code to track the pill dispensing device over its lifecycle.

According to yet other examples, the processor of the pill dispensing device may be configured to execute a geo-aware function to determine and report a location of the pill dispensing device based on one or more of a global positioning service and a network based location determination. The geo-aware function of the pill dispensing device may include one or more of inventory tracking and environmental monitoring. The pill dispensing device may include biometric identification features to verify an identity of a user interacting with the pill dispensing device. The pill pack may be integrated within the housing of the pill dispensing device such that the pill pack cannot be removed. A plurality of holes may be formed in the housing of the pill dispensing device to match a location of each pill within the pill pack. The housing of the pill dispensing device may be configured to accommodate a plurality of pill packs within an interior section of the housing. The plurality of pill packs are configured to interlock in the housing.

According to some embodiments, a communication system of a pill dispensing device is provided to facilitate communication with one or more sources. The communication system may include an audiovisual component integrated within the pill dispensing device including an electronic ink display configured to provide a graphical user interface (GUI), and a microphone and one or more speakers. The communication system may also include a processor of the pill dispensing device configured to collect and store data associated with one or more of pill consumption and a user, and a server in electronic communication with the audiovisual component. The server may be configured to notify the processor to display information to the user through the GUI and/or another computing device associated with the user, and provide at least a portion of user information received from the processor to a third party.

According to other examples, the processor of the communication system may be configured to collect medical information about the user via input by the user through the GUI. The audiovisual component of the communication system may be configured to accept input provided by one or more of: a keyboard, a mouse, a touch interface, an optically captures gesture, an eye-tracking mechanism, a pen, or a gyroscopic input mechanism. The processor of the communication system may also be configured to collect medical information about the user via communication with one or more health monitoring devices. The processor of the communication system may be configured to collect pill consumption information about the user. The server may be configured to provide the collected medical and pill consumption information about the user to the third party. The server may be configured to receive medical information from the third party and provide the processor to display the information through the GUI. The GUI of the communication system may be configured to display one or more of an alert to remind the user to consume a pill, an instruction associated with the pill, and information received from the third party. A timing and a type of the alert may be preprogrammed based on an observed behavior analysis of the user. At least one of a time and a type of the alert may be customizable.

According to further examples, the server may be configured to automatically alert the third party if a user fails to remove a pill from the pill pack at a predetermined time. The server may be further configured to automatically alert the third party when the pill pack is one or more of almost empty and expired. The server may also be configured to electronically communicate with the audiovisual component and the processor employing one or more of a cellular wireless communication, an optical communication, a near field communication, a wireless local area network communication, and a wide area network communication.

According to yet other examples, one or more subcomponents of the audiovisual component and the processor of the communication system may be powered through solar cells integrated into the pill dispensing device. The electronic ink display of the communication system may be bistable enabling low power consumption. The electronic ink display may include charged particles dispersed in a liquid. The charged particles dispersed in the liquid are deposited on a back side of the display between two parallel conductive plates. A voltage may be applied to the conductive plates causing the charged particles to polarize. The conductive plates may be divided into pixels to enable polarization of the charged particles pixel by pixel to form text and images on the display. The electronic ink display may also be configured to enable video display by employing pixel by pixel dithering. The electronic ink display may further include an LED blinking light feature and a vibrating feature.

According to some embodiments, a pill consumption detection system integrated with a pill dispensing device is provided. The detection system may include a trace diagram comprised of one or more conductive ink traces printed on a pill pack configured to detect a modification to the pill pack, an electronic connection from the trace diagram to circuitry of the pill dispensing device, and a processor in electronic communication with the circuitry of the pill dispensing device configured to collect pill consumption information about a user.

According to other examples, a location of each pill in the pill pack may be tagged with a conductive ink trace. A connection of the one or more conductive ink traces may be severed when a pill is removed from the pill pack. A new connection may be established in the one or more conductive ink traces when a pill is removed from the pill pack. A resistance change in the one or more conductive ink traces may be measured to detect when a pill is removed from the pill pack. One or more of optical sensing and/or pressure sensing may be employed to detect when a pill is removed from the pill pack. The one or more conductive ink traces may be employed to detect an opening and closing of movable parts of the pill dispensing device. The conductive ink may be printed on a substrate and the substrate is attached to the pill pack. An ink jet printing technology may be employed to print the conductive ink on the substrate.

According to further examples, the conductive ink may be printed directly on a backing of the pill pack. The conductive ink may be layered between non-conductive layers. A tag may be employed to track removal of each pill from the pill pack. Connecting each pill may be placed over one or more conductive traces and a magnet is incorporated on an opposite side of the conductive traces to maintain the tags in place and to resist a spring effect.

According to some embodiments, a method of manufacturing a pill pack with an integrated detection system incorporated with a pill dispensing device is provided. The method includes creating a trace diagram, printing a printout of the trace diagram on a biodegradable substrate, and connecting the conductive printout of the trace diagram to at least one of: a backing of the pill pack integrated with the pill dispensing device and a circuitry of the pill dispensing device. The method further includes assembling the biodegradable substrate with the conductive printout, the pill pack, circuitry, a display, and at least one sensor in a biodegradable housing, preprogramming the circuitry of the pill dispensing device with one or more of user specific data and a notification application, and printing the printout of the trace diagram using a 3D (three dimensional) printer. The method further includes printing the printout of the trace diagram using an inkjet printer, printing the printout of the trace diagram using electrically conductive ink, printing the printout of the trace diagram on a backing of the pill pack, and connecting the printout of the trace diagram to the circuitry by one or more of epoxy and solder.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g. as one or more programs running on one or more microprocessors), as firmware, or as virtually any combination thereof, and that designing the circuitry and/or writing the code for the software and/or firmware would be well within the skill of one of skill in the art in light of this disclosure.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a hard disk drive (HDD), a computer memory, etc.; and a transmission type medium such as a digital and/or an analog communication medium (e.g., a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity of gantry systems; control motors for moving and/or adjusting components and/or quantities).

A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 5, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A pill dispenser device, comprising:
   a memory adapted to store instructions;
   a processor coupled to the memory and adapted to execute the instructions stored on the memory;
   a communication module coupled to the processor and configured to facilitate communication with one or more sources to exchange pill consumption and user data, wherein the one or more sources include external sources, and wherein the communication module is configured to transmit customized advertisements, which are based on the pill consumption and the user data and which are provided from the external sources, to the pill dispenser device to be displayed;
   a printed circuit board adapted to support one or more of the memory, the processor, and circuitry associated with operations of the pill dispenser device;
   a display in the electronic communication with the memory, the processor, and the circuitry;
   a trigger device configured to activate a signal to destroy user data stored on the pill dispenser device;
   a pill pack that includes a plurality of pharmaceutical pills, wherein the processor is adapted to monitor a removal of the pharmaceutical pills from the pill pack; and
   a housing that includes one or more of the memory, the processor, the communication module, the printed circuit board, the display, and the pill pack.

2. The pill dispenser device of claim 1, wherein one or more of the memory, the processor, the printed circuit board, the display, and the housing include a biodegradable compound selected from: plastics, polymers, starch-based materials, wood, plant based fiber products, or paper products, and wherein a common feature of the compound includes being compostable.

3. The pill dispenser device of claim 1, wherein the trigger device is further configured to accelerate biodegradation of the pill dispenser device.

4. The pill dispenser device of claim 1, wherein the processor is preprogrammed by a distributor with one or more of user specific data and a customized notification application.

5. The pill dispenser device of claim 1, wherein the pill dispenser device is configured to collect one or more of pill consumption information about a user and medical information about the user via input by the user or communication with one or more health monitor devices.

6. The pill dispenser device of claim 1, further comprising or more of: an RFID tag, a QR code, and a bar code to track the pill dispenser device over its lifecycle.

7. The pill dispenser device of claim 1, wherein the processor is configured to execute a geo-aware function to determine and report a location of the pill dispenser device based on one or more of a global positioning service and a network based location determination.

8. The pill dispenser device of claim 1, wherein the pill dispenser device includes biometric identification features to verify an identity of a user that interacts with the pill dispenser device.

9. The pill dispenser device of claim 1, wherein a plurality of holes are formed in the housing to match a location of each pill within the pill pack.

10. The pill dispenser device of claim 1, wherein the communication module is further configured to transmit a survey or a questionnaire from the external sources to the pill dispenser device for population and integration with the pill consumption and the user data.

11. A communication system of a pill dispenser device to facilitate communication with one or more sources, the communication system comprising:
- an audiovisual component integrated within the pill dispenser device and comprising:
  - an electronic ink display configured to provide a graphical user interface (GUI); and
  - one or more speakers;
- a processor of the pill dispenser device configured to collect and store data associated with one or more of pill consumption and a user, wherein the stored data is erasable in response to activation of a trigger, and wherein the trigger includes one or more of a compound, a chemical agent, or an electrical signal; and
- a server in communication with the processor and the audiovisual component, wherein the server is configured to:
  - notify the processor to display information to the user through the GUI and/or another computing device associated with the user, wherein the displayed information includes one or more of an alert to remind the user to consume a pill, an instruction associated with the pill, and information received from a third party;
  - obtain information representative of a behavior of the user over a particular period of time to determine when the user tends to take the pill, wherein:
    - the obtained information includes the data associated with one or more of pill consumption and the user,
    - the server is configured to automatically program the alert, based on the obtained information to remind the user to consume the pill, and
    - subsequent pill dispenser devices are provided to the user with the alert pre-programmed to correspond to the behavior of the user such that the subsequent pill dispenser devices omit having to obtain the information representative of the behavior of the user in order to program the alert; and
  - provide, to the third party, at least a portion of the data associated with one or more of pill consumption and the user that is collected and stored by the processor.

12. The communication system of claim 11, wherein a timing and a type of the alert is based on the behavior of the user.

13. The communication system of claim 11, wherein the server is configured to automatically alert the third party if the user fails to remove the pill from a pill pack housed within the pill dispenser device at a particular time or when the pill pack is one or more of: almost empty and expired.

14. The communication system of claim 11, wherein the electronic ink display includes charged particles dispersed in a liquid that are deposited on a back side of the electronic ink display between two parallel conductive plates.

15. The communication system of claim 14, wherein the conductive plates are divided into pixels to enable, in response to application of a voltage to the conductive plates, polarization of the charged particles pixel by pixel to form text and images on the electronic ink display.

16. A pill consumption detection system integrated with a pill dispenser device, the detection system comprising:
- a trace diagram that includes one or more conductive ink traces printed on a pill pack configured to detect a modification to the pill pack, wherein a location of each pill in the pill pack is tagged with a conductive ink trace such that:
  - removal of each respective pill from the pill pack is detected through the conductive ink trace, and
  - an opening and a closing of one or more halves of the pill dispenser device that join to form the pill dispenser device is detected through the one or more conductive ink traces to monitor for tampering of the pill dispenser device;
- an electronic connection from the trace diagram to circuitry of the pill dispenser device; and
- a processor in electronic communication with the circuitry of the pill device and configured to collect pill consumption information about a user, wherein the collected pill consumption information is erasable in response to activation of a trigger, and wherein the trigger includes one or more of a compound, a chemical agent, or an electrical signal.

17. The detection system of claim 16, wherein a connection of the one or more conductive ink traces is severed and a new connection is established after a pill is removed from the pill pack.

18. The detection system of claim 16, wherein the processor is configured to measure or sense, via optical sensing or pressure sensing, one of a resistance change in the one or more conductive ink traces to detect whether a pill is removed from the pill pack.

19. The detection system of claim 16, wherein the conductive ink includes one of: printed on a substrate and the substrate is attached to the pill pack, or printed directly on a backing of the pill pack.

20. The detection system of claim 16, further comprising a tag to track removal of each pill from the pill pack.

* * * * *

UNITED STATES PATENT AND TRADEMARK OFFICE
CERTIFICATE OF CORRECTION

PATENT NO. : 9,760,691 B2
APPLICATION NO. : 14/647079
DATED : September 12, 2017
INVENTOR(S) : Seeger It is certified that error appears in the above-identified patent and that said Letters Patent is hereby corrected as shown below:

In the Specification

In Column 2, Line 57, delete "device:" and insert -- device; --, therefor.

In the Claims

In Column 22, Line 61, in Claim 6, delete "or more" and insert -- one or more --, therefor.

Signed and Sealed this
Eighth Day of May, 2018

Andrei Iancu
*Director of the United States Patent and Trademark Office*